(12) United States Patent
Koch et al.

(10) Patent No.: US 8,808,343 B2
(45) Date of Patent: Aug. 19, 2014

(54) DEVICE FOR PREDICTING A BODY TEMPERATURE OF A PATIENT

(75) Inventors: Jochim Koch, Ratzeburg (DE); Maral Haar, Hamburg (DE); Susanne Stahlkopf, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 689 days.

(21) Appl. No.: 12/487,829

(22) Filed: Jun. 19, 2009

(65) Prior Publication Data
US 2009/0319009 A1    Dec. 24, 2009

(30) Foreign Application Priority Data

Jun. 21, 2008  (DE) .......................... 10 2008 029 579
Nov. 25, 2008  (DE) .......................... 10 2008 058 968

(51) Int. Cl.
*A61F 7/00*  (2006.01)
*A61B 5/01*  (2006.01)

(52) U.S. Cl.
USPC ........................................... 607/96; 600/549

(58) Field of Classification Search
USPC ........................................... 607/96; 600/549
See application file for complete search history.

(56) References Cited

U.S. PATENT DOCUMENTS

| | | | | |
|---|---|---|---|---|
| 4,638,436 | A * | 1/1987 | Badger et al. | 607/102 |
| 2004/0133081 | A1 * | 7/2004 | Teller et al. | 600/300 |
| 2005/0101872 | A1 * | 5/2005 | Sattler et al. | 600/483 |
| 2006/0243720 | A1 | 11/2006 | Koch et al. | |
| 2009/0099629 | A1 * | 4/2009 | Carson et al. | 607/96 |

FOREIGN PATENT DOCUMENTS

DE    10 2005 019 472 A1    11/2006

OTHER PUBLICATIONS

Fiala, D.; Lomas, K. J.; Stohrer, M.: Computer prediction of human thermoregulatory and temperature responses to a wide range of environmental conditions. In: International Journal of Biometeorology. Springer Verlag Berlin/Heidelberg. 2001. vol. 45. Nr. 3. pp. 143-159—ISSN 0020-7128.

Lyon A. J.; Oxyley C.: HeatBalance, a computer program to determine optimum incubator air temperature and humidity. A comparison against nurse settings for infants less than 29 weeks gestation. In: Early Human Development, vol. 62, Nr. 1, May 2001, pp. 33-41—ISSN 0378-3782.

* cited by examiner

*Primary Examiner* — Lee S Cohen
(74) *Attorney, Agent, or Firm* — McGlew and Tuttle, P.C.

(57) ABSTRACT

A device (5) is provided for predicting or simulating a body temperature of a patient (P) at a point in time that is in the future. The device includes a device for determining parameter values concerning the patient (P) and/or the environment thereof. A computing device is provided for simulating a body temperature of the patient (P). A process and a workstation. Are also provided.

21 Claims, 3 Drawing Sheets

DEVICE FOR PREDICTING A BODY TEMPERATURE OF A PATIENT

CROSS REFERENCE TO RELATED APPLICATIONS

This application claims the benefit of priority under 35 U.S.C. §119 of German Patent Application DE 10 2008 029 579.5 filed Jun. 21, 2008 and DE 10 2008 058 968.3 filed Nov. 25, 2008, the entire contents of each of which are incorporated herein by reference.

FIELD OF THE INVENTION

The present invention pertains to a device for predicting a body temperature of a patient according. The present invention also pertains to a process and to a workstation.

BACKGROUND OF THE INVENTION

The temperature of operating rooms is usually stabilized at 20° C. The patient is stripped of clothing or is covered only partly by means of a light surgical cover during the procedure. The patient is fully exposed in the area of the actual region of surgery. Additional heat losses may develop during major abdominal surgery due to the larger area and due to the heat of evaporation of the exposed organs. Patients therefore cool down without suitable countermeasures during the surgery, doing so approximately by 1° C. per hour in the first 3 hours. Cooling begins already when the patients leave the heating bed and are prepared for the surgery.

Thermotherapy measures, which shall maintain the body temperature at a preset level or shall bring it to a preset level are used to prevent the cooling and above all undercooling (hypothermia) of the patient. Only few patients are kept warm by additional thermotherapy devices during the surgery even now because of lack of awareness of the problem, which is frequently associated with an unplanned cooling and may lead to considerable health consequences for the patient and to economic losses to the hospital.

The extent to which the particular patient loses temperature and how intensive the counteracting heat supply measures must be are nevertheless unknown.

SUMMARY OF THE INVENTION

An object of the present invention is to provide a device for predicting a body temperature of a patient at a point in time that is in the future.

According to the invention, a device is provided for predicting or simulating a body temperature of a patient at a point in time that is in the future. The device has at least one means for determining parameter values concerning the patient and/or the environment thereof. It has, furthermore, a computing means for simulating a body temperature of the patient.

A "parameter value" of the patient is defined according to the present invention, for example, as the age of the patient, his or her sex, his or her height as well as his or her body weight. Some of these values already appear—often also in the electronic form—from the existing patient files. Further parameters may concern the patient's metabolism, a physiological function of the blood flow regulation between central organs and the periphery, and the initial body temperature at the beginning of the examination, regardless of the how it is measured, etc.

Parameter values that concern the patient's environment are defined according to the present invention, for example, as ambient temperature, ambient humidity, infusion flow in case of an infusion, temperature of the infused medium, respiratory minute volume set, breath temperature, effect of anesthetics, duration of the surgery and the like. Some of these data are already known before the surgery. These include, for example, the mean duration of the surgery in case of standard procedures. Further parameters are the extent of coverage of the body surface by means of drapes or the heat output of therapy devices.

"Determination" of parameter values is defined according to the present invention as both the reading, measurement, reaching, estimation, etc., of parameter values. An input by means of an input device in the device according to the present invention or the means for determining parameter values are also defined as "determination" according to the present invention.

"Simulation" of a body temperature of the patient is defined especially as simulation based on the determined parameter values of the patient and/or of the environment thereof. The simulation values may concern a point in time in the past and/or points in time in the future. The aforementioned points in time may be set as fixed points in time, but they may also be variable. The distances between individual points in time may depend especially on events, e.g., a recognized deviation of a simulated temperature value from a temperature reference value.

It is possible by means of the simulation program used in the computing means to simulate the body temperature of an individual patient. The caregiver responsible for the patient's care can thus, among others, be advantageously enabled to estimate before the surgery to what extent the body temperature can drop during the scheduled surgery without a countermeasure or with possible countermeasures. The timely recognition of the onset of undesired body temperatures and the taking of appropriate heating measures are advantageously made possible hereby. Using the device according to the present invention, the person in charge is able to plan the surgery concerning the duration and the patient's temperature profile such that it will be more tolerable for the patient. Furthermore, it is possible to optimize the use of the available thermotherapy measures. After effects of cooling of the patient during the surgery, such as delayed wound healing, risk of bleeding, prolonged hospital stay as well as —in case of pronounced cooling —trembling caused by cold, which is unpleasant and often also painful for the patient, can thus be anticipated and therefore avoided or at least reduced in advance. This is associated with considerable cost savings for the health care institution in which the procedure is carried out and with the possibility of better allocation of resources in health care. On the whole, the patient's rehabilitation can be improved more rapidly postoperatively and the patient will have a better memory of the surgery.

It is thus possible by means of the device according to the present invention when used as a planning tool to recognize the course of the expected body temperature before the surgery and to make preparations for suitable heating measures or to check measures already being contemplated.

When using the device according to the present invention outside the operating room or at comparable locations or outside patient therapy, it is, furthermore, possible to make available a prognostic tool to medical staff, such as physicians and caregivers, by means of which these can develop increased awareness that the patient may cool down and practice the taking of appropriate measures. The device according to the present invention can therefore be advantageously used as a simulation tool for educating and training health care staff and physicians. However, it also leads, quasi as an incidental benefit, when used during the surgery proper, to increasing the awareness of the problem of perioperative hypothermia.

The device according to the present invention is also advantageously suitable for applications other than those taking place in the operating room or occurring in time before or after the stay in the operating room. It is suitable for the above-mentioned purposes, for example, also for use in the wake-up room or in the intensive care unit (ICU) and whenever heating, cooling or repeated heating of the patient is concerned. The planning and monitoring accompaniment of an intended cooling in the sense of an intended hypothermia, of whatever degree it may be, is advantageously also possible with the device according to the present invention.

The simulation may be carried out by means of a corresponding software program, which was created to simulate the body temperature over time, for example, on the basis of physical and physiological algorithms.

The software program may be able to be carried out, for example, by means of a PC (personal computer). This PC may be a conventional desktop PC, for example, for planning the surgery. However, already existing, PC-based devices (as they are used, for example, in the recovery-room, in the operating room or in the intensive care unit) may also be used at the patient.

The device according to the present invention may advantageously also be used as a planning tool for the question of the postoperative reheating or temperature maintenance. The above-mentioned advantages can be achieved to the full extent.

Thus, it is proposed in an embodiment according to the present invention that the device be provided with a means for detecting the body temperature of the patient. The means for detecting the body temperature may be a means for measuring the armpit temperature, rectal temperature, temperature within a blood vessel, temperature measured at the eardrum, etc.

The body temperatures may be measured online by invasive or noninvasive temperature sensors, and they may be measured continuously or intermittently. Measurement by the staff is also considered according to the present invention. In case of automated measurement of the temperatures, this is carried out usually with a patient monitor. This usually has two or more temperature channels.

By determining the real temperature of the patient, it is possible according to the present invention to use an actual temperature value, which likewise affects the simulation, for the further simulation for the benefit of the patient.

In yet another preferred embodiment, the device according to the present invention has a means for comparing the detected body temperature to the simulated body temperature.

It is thus possible to continually compare the measured-real-body temperature online with the simulated temperature values, while unexpected deviations can be displayed very rapidly before the patient does indeed experience this temperature deviation or temperature drop. Embedding in ongoing alarms is possible according to the present invention. It is likewise possible to send instructions when the current heating measures are no longer sufficient according to the simulated course, possibly compared to the real values. It is possible to display these data and instructions at the beginning of a surgery in the form of a review. The measures that are suitable for different operating times may appear from the display. In addition, instructions can be sent during the surgery when the temperature threatens to drop. A rapid intervention by the staff and/or device is thus possible.

In yet another preferred embodiment according to the present invention, the device according to the present invention has at least one output means for outputting events of the determination and/or simulation and/or comparison of the simulated data with the real data. Based on this output means, recommendations can be displayed, alarms can be outputted or set points can be sent for thermotherapy devices. The device according to the present invention is thus used for increased safety, it relieves the person responsible of decision-making processes and can limit the possibility of human errors in decisions. It can preset set points for the person responsible, by means of which the connected warming therapy devices can be operated.

In another preferred embodiment, the device according to the present invention has a means for controlling and/or regulating heating means based on the simulated body temperature values or the preset set points and/or characteristics. It is thus possible to use a closed-loop control for the heating means. This in turn relieves the attending physician or caregiver and can increase or facilitate the safety of the patient intraoperatively, especially in moments of stress, as well as the postoperative healing of the patient.

A further object of the present invention is also accomplished by the process having and by a workstation. Since the above-mentioned advantages can thus be achieved to the full extent, reference is expressly made here to the above discussion thereof to avoid repetitions.

The present invention will be explained in more detail below on the basis of the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
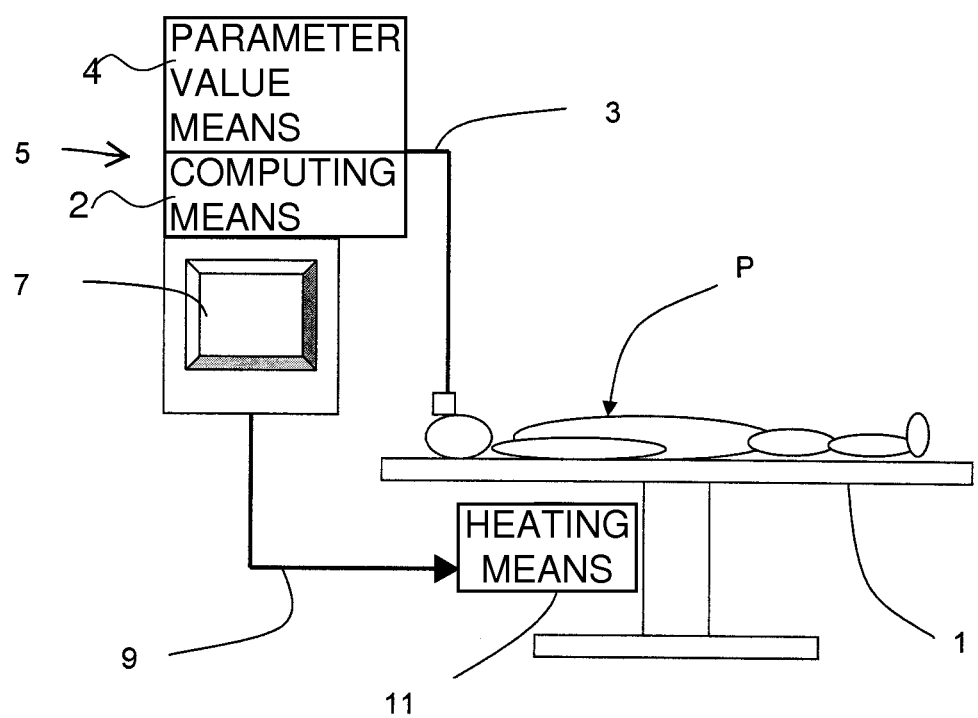
FIG. 1 is a schematic view showing an anesthesia workstation with a device according to the present invention in a simplified form.

Referring to the drawings in particular, FIG. 1 shows a patient P lying on an operating table 1. The patient P is connected to the device 5 according to the present invention for predicting a body temperature by means of a temperature measuring line 3. Device 5 comprises a parameter value means/device 4, for determining parameter values of the patient P, which may include, for example, measured temperature signals transmitted by means of the temperature measuring line 3. Device 5 also includes a computing means/device 2 simulating a future body temperature based on the parameters. Device 5 comprises, furthermore, a monitor 7 for displaying the simulation results. The results of the simulation are transmitted by means of a data line 9 to a heating means 11.

Figure 2:
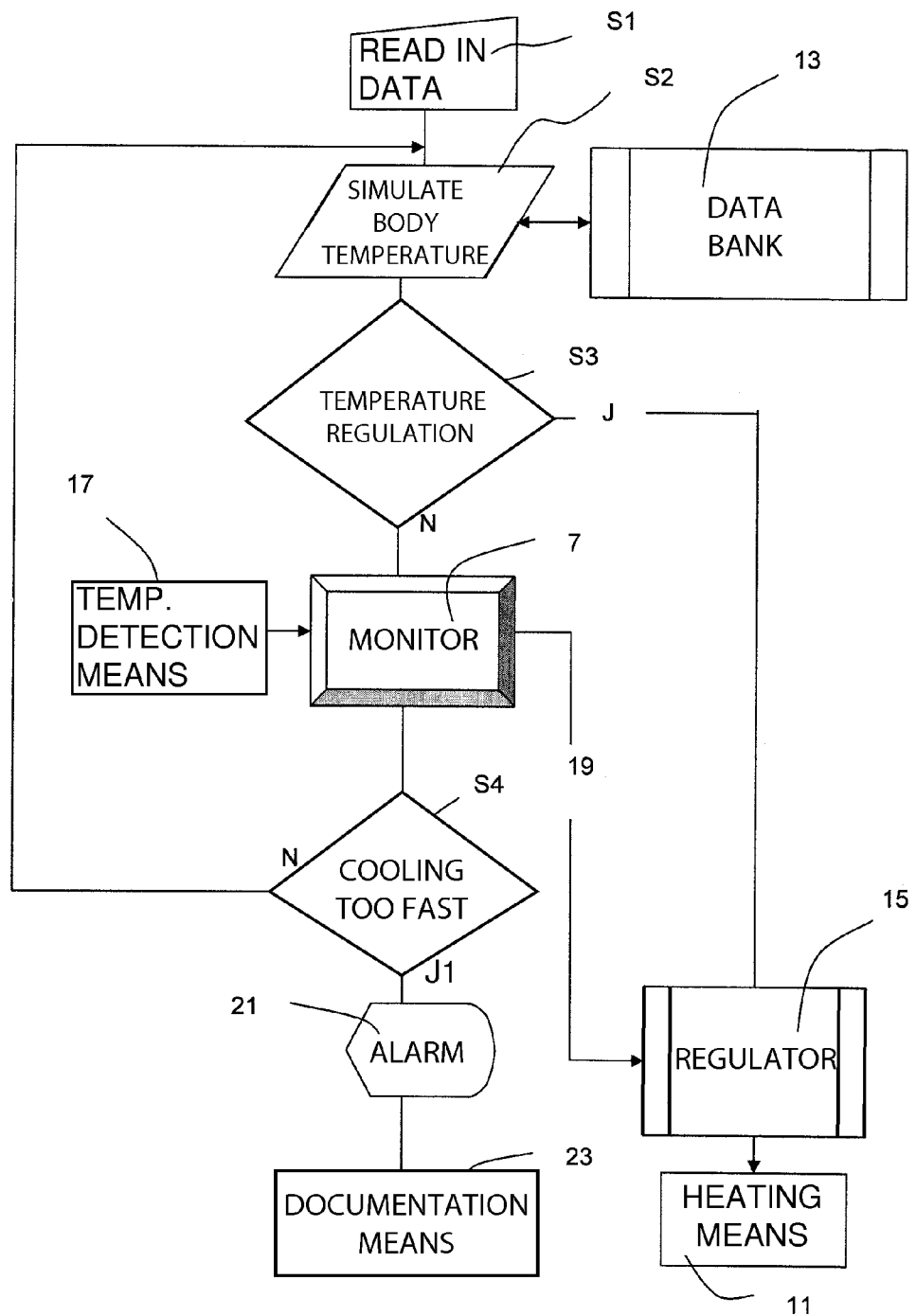
FIG. 2 is a view showing a possible process when the device according to the present invention is integrated in a patient temperature management.

FIG. 2 shows the integration of the device according to the present invention in a heat management process of a patient, not shown in FIG. 2. The data and parameter values necessary for a simulation are entered or automatically read in by the system in a first step S1.

Simulation of the body temperature for points in time in the future is performed in a subsequent step S2. Algorithms and information on physiological models of thermoregulation, which are stored in a data bank 13, are taken into account here.

A decision is made in the next step S3 on whether a thermotherapy (raising or lowering of the temperature) is necessary. If the result is obtained here that a temperature regulation is necessary (case "J"), a recommendation is sent or a direct actuation of the device is performed. The devices can be actuated by means of a regulator 15, which controls or regulates, for example, a thermotherapy means 11. The result of a temperature measurement by means of temperature measuring means 17 is displayed on the monitor 7, and the outputted temperature signal can be sent to the regulator 15 by means of the data line 19. Regulator 15 carries out comparisons between the temperature values sought to be reached in step S3 and the real temperature values measured by means of the temperature measuring means 17. Compensation of the difference between these values is sought to be achieved by means of the heating means 11.

A decision is made in a next step on whether a trend analysis, which may be stored with a plausibility check, for example, in the data bank 13, shows that the patient is cooling down faster or more intensely than expected. An alarm is sent by means of an alarm means 21 in the positive case "J1" and this is documented by means of a documentation means 23.

The regulation shown in FIG. 2 is an example of a closed-loop regulation. Instead of such a regulation, it is, of course, also possible to provide a manual regulation by the caregiver in charge.

For example, the following procedure, which was successfully carried out by the applicant, is suitable for simulating the body temperature. Different formulas for the radiant, convective, conductive and evaporative heat release will be described below. The evaporation of disinfectants on the skin and the heat losses via open wounds are likewise explained. The dot is used in the equations to represent breaks.

Heat Radiation

The heat release from warm to cold bodies via long-wave infrared radiation is described by Equation 1:

$$P\text{radiaton} = \sigma \cdot A \cdot e \cdot (T_S^4 - T_A^4), \quad (1)$$

in which
Pradiation: [W], radiation losses,
$\sigma = 5.67 \cdot 10^{-8}$ [Wm$^{-2}$K$^4$], Stefan-Boltzmann constant.
A: [m$^2$], total skin surface area,
e=1, radiation coefficient of the body,
$T_S$: [K], skin temperature,
$T_A$: [K], ambient temperature.

The Stefan-Boltzmann law (Equation 1) can be further specialized for use in a simulation program.

Since the physiological model being considered is divided into a simulation program in the core and one in the periphery (extremities), there can be two different equations for the heat release by radiation.

In addition, it can be borne in mind that the heat release to the environment differs according to release to the wall (40%) and to the ceiling (60%). Finally, it is also possible to introduce into the equation a factor for the percentage of the body that loses heat by radiation, convection and transepidermal losses of water.

The modified Equation 1 for the radiation losses via the core of the body will then have, for example, the following form:

$$P\text{raditionCore} = a\text{Conv} \cdot a\text{Core} \cdot A \cdot \sigma \cdot (0.4 \cdot ((T k\text{skin} + 273.15)^4 - (T\text{wall}+273.15)^4) + 0.6 \cdot ((T k\text{skin} + 273.15)^4 - (T\text{ceiling}+273.15)^4)) \quad (2)$$

in which:
PradiationCore: [W], radiation losses via the core,
aConv: percentage of the body that releases heat by convection, radiation and transepidermal losses of water, mostly 70%,
aCore: percentage of the weight of the body core, mostly 60%,
aPeri: percentage of weight of the body periphery/extremities,
Tkskin: [° C.] near-core skin temperature for the body surface lying on top (releasing heat by convection),
Tpskin: [° C.] skin temperature near the extremities for the body surface lying on top,
Twall: [° C.] temperature of room wall,
Tceiling: [° C.] temperature of the ceiling of the room.

A similar equation can be set up for the periphery. The heat release by radiation can now be calculated in a simulation program with these modified equations of the Stefan-Boltzmann law.

Convection

The release of heat by convection depends on the difference between the skin temperature and the ambient temperature as well as on the body surface participating in the exchange and is described by:

$$P\text{Convection} = h_c \cdot (T_S - T_A) \cdot A \quad (3)$$

The convection coefficient $h_c$ necessary for Equation 3 depends on the motion of the air and is calculated below:

$$h_c = 7.9 \cdot FLR^{0.5} \quad (4)$$

in which FLR is the motion of air in meters per second.

Just as in the case of the radiation losses, distinction must be made between the core and periphery or extremities in this case as well, so that Equation 3 must be divided into the core part (aCore) and the periphery part (aPeri). Since the patient is lying on an operating table in the operating room, factor aConv is additionally introduced into Equation 3 as well. To obtain the same unit [W] for all heat losses to be calculated, a division by 0.86 is finally performed. The final calculation formula will then be as follows:

$$P\text{convection} = \frac{7.9 \cdot FLR^{0.5} \cdot A \cdot a\text{Conv} \cdot (a\text{Core} \cdot (Tk\text{skin} - T_A) + a\text{Peri} \cdot (Tp\text{skin} - T_A))}{0.86} \quad (5)$$

Conduction

Heat release by conduction to adjacent, cold materials at the body is dependent on the contact material and the conductivity thereof as well as on the size of the contact surface.

$$P\text{conduction} = h_c \cdot (T_S - T_{Ob}) \cdot A_c \quad (6)$$

Here, $T_{Ob}$ [°C.] is the temperature of the adjacent material, $h_c$ [W/m²°C.] is the conductivity of the contact material, and $A_c$ [m²] is the part of the body surface that releases heat by conduction.

Since the core and periphery are considered separately in the simulation program, the above formula for the calculation program must be divided into two equations. The term (A−aCond) is used for the variable $A_k$ used in Formula 6 and aCond: [%] represents the part of the surface that participates in the heat exchange by conduction. Thus, the following equations are integrated in the program for the core loss and peripheral loss:

$$PconductionCore = h_c \cdot (Tcore - T_{Ob}) \cdot A \cdot aCond \cdot aCore$$

and $$PconditionPeri = h_c \cdot (Tperi - T_{Ob}) \cdot A \cdot aCond \cdot aPeri \qquad (7)$$

wherein Tcore: [°C.] is the core temperature and Tperi: [°C.] is the peripheral or extremity temperature.

Evaporation

Ultmann's calculation formula for the insensible transepidermal water losses Ptwl: [W] is as follows:

$$Ptwl = k \cdot A \cdot aConv \cdot \left(ps - \frac{TrF}{100} \cdot pa\right) \cdot \frac{2400}{3600} \qquad (8)$$

The variable k [g/(h·m²·kPa)] is the coefficient of permeability of the skin and is calculated here for children as a function of their gestational age [weeks] and their postnatal age (age: [months]). The formula for this factor is:

$$k = 1.5 \cdot \left(1 + \frac{2 \cdot k01 - 3}{2 + \text{age}}\right) \cdot e^{9.119 - \frac{2809}{273.15 + T_S}} \qquad (9)$$

Variable k01 contains the dependence on the gestational age of the infant. If the number of weeks of pregnancy is greater than 35, k01=1.3. As soon as the value of the gestational age is less than 35, the value is calculated as follows:

$$k01 = 24000 \cdot e^{-0.281 \cdot \text{gestational age}} \qquad (10)$$

The value for the coefficient of permeability for adults is $6.1 \cdot 10^{-4}$ [kg/(h·m²·mmHg)] or 4.575 [g/(h·m²·kPa)].

Factor aConv is also present in Equation 8, because water is released only by the surface that does not lie on the operating table.

The variables ps and pa from Equation 8 are the water vapor, pressures of the skin (ps) and of the air (pa) in [kPa] and can be calculated as follows:

$$ps = e^{6.9078 \cdot 10^{-5} \cdot \frac{-1710764 + 236387 \cdot T_S}{228 + T_S}} \qquad (11)$$

and $$pa = e^{6.9078 \cdot 10^{-5} \cdot \frac{-1710764 + 236387 \cdot T_A}{228 + T_A}} \qquad (12)$$

Factor TrF in Formula 8 is the relative humidity of the environment in %.

The overall heat release of the respiratory heat losses depends on the metabolism, the respiratory minute volume, the partial pressures (in the body and in the environment) as well as the humidity of the ambient air. To determine the water consumption, the convective losses (PConvresp: [W]) and the evaporative losses (Pevaresp: [W]) in the lungs are calculated.

Analytical and physical equations were set up in the applicant's basic development specifically for the respiratory heat losses.

The overall heat release is dependent here on the metabolism, respiratory minute volume, partial pressures (in the body and in the environment), as well as on humidity of the air of the environment. To determine the water consumption, the losses via the convective pathway (PConvresp: [W]) and the evaporative pathway (Pevaresp: [W]) in the lungs are calculated.

The cooling output due to the convection is calculated as follows:

$$Pconvresp = AMV\text{meta} \cdot \rho 50 \cdot cair \cdot (T_{Lung} - T_A) \qquad (13)$$

AMVmeta: [L/min] is composed of the component that participates in the gas exchange in the lungs and the amount of air that remains in the gas-carrying system during inspiration and is expired without having participated in the gas exchange (dead space ventilation).

The oxygen consumption, which depends on the metabolism, is additionally needed to calculate the quantity that is inspired and participates in the gas exchange in the alveoli. One L of $O_2$ consumption corresponds to 20 kJ of heat released by the body. In case of an energy production (Pmeta) of about 83.3 W (the metabolism corresponds to a 30-year-old man with a body weight of 73 kg and a height of 1.79 m), the oxygen consumption now equals 0.25 L per minute.

$$VO_2 = Pmeta \cdot \frac{1}{20} \qquad (14)$$

A ventilation of 5 L/minute is obtained for the respiratory minute volume (AMV: [L/min]) according to Equation 15 without regard to the dead space respiration.

$$AMV = \frac{VO_2 \cdot 100}{21\% - 16\%} \qquad (15)$$

To determine the complete heat losses via the respiratory tract now, the dead space ventilation must be included as well. The dead space volume can also be determined explicitly to determine the quantity.

On the one hand, this component is set at 30% for simplicity's sake. The respiratory minute volume determined equals 7.1 L/minute here. On the other hand, the dead space volume can also be determined explicitly. For the above-described person, the volume equals according to a rule of estimation: 2 mL per kg of body weight correspond to the dead space ventilation [10], approx. 150 mL. In addition, the respiration rate is taken into account for the calculation here. A total respiratory minute volume of about 7.25 L/minute is then obtained for an adult with a respiration rate of 15 breaths per minute.

The convective-respiratory heat losses can now be determined with AMVmeta determined by means of Equation 13. A value of 1.662 W is obtained with the following parameters:
AMVmeta=7.25: [L/min] respiratory minute volume (with dead space),
ρ50=1.057: [kg/m³] density of air at 50° C.,
cair=0.310: [kcal/(kg·K)] specific heat of air,
$T_{Lung}$=37: [°C.] temperature in the lung (near the core),
$T_A$=23: [°C.] ambient temperature.

The evaporative heat loss component is calculated from the heat of evaporation of water in the lungs ($q_{lung}$: [kJ/kg]) and from the quantity of evaporated water [W·kg/L], i.e., from the difference between the absolute inspired humidity ($md_{Air}$) and the expired humidity ($md_{Lung}$):

$$Pevarresp = (md_{Lung} - md_{air}) \cdot qlung \quad (16)$$

the total breathing humidities and heat of evaporation in the lungs are calculated below in Equations 17, 18 and 19:

$$md_{Lung} = AMV \cdot \frac{P_{Lung}}{puat} \cdot \frac{18 \cdot 10^{-3} [kg]}{24[l]} \quad (17)$$

$$md_{Air} = AMV \cdot \frac{P_{Air}}{puat} \cdot \frac{18 \cdot 10^{-3} [kg]}{24[l]} \quad (18)$$

$$q_{Lung} = q0 - \frac{q0 - q100}{100} \cdot T_{Lung} \quad (19)$$

The constants occurring in Equation 19 are the heat of evaporation at 0° C.: q0=604: [kcal/kg] and at 100° C.: q100=538: [kcal/kg].

The unknown factors in Formulas 17 ($p_{lung}$) and 18 ($p_{Air}$) are the partial pressures in the lungs and in the air, respectively. The constant puat is the prevailing ambient pressure. The partial pressure in the lungs ($p_{Lung}$: [atm]) is obtained from the following calculation formula:

$$PLung = \frac{rF_{Lung}}{100[\%]} \cdot po \cdot e^{qLung \cdot 427 \left[\frac{kp \cdot m}{kcal}\right] \frac{T_{Lung} - To}{Rd \cdot To \cdot T_{Lung}}} \quad (20)$$

in which: $rF_{Lunge}$=100: [%] is humidity of the expired air, po=0.03: [atm] is the pressure at the temperature reference value, To=23.772: [° C.] is the temperature reference value from the steam table, and Rd=47.06: [(kp·m)/(kg·k)] is the gas constant for vapor.

To determine the partial pressure of air, the humidity in the expired air ($rF_{Air}$) must be replaced in Equation 21 with the inspired humidity ($rF_{Air}$=50: [%]) as well as the temperature in the lungs ($T_{Lung}$) must be replaced with the ambient temperature ($T_A$).

The heat of evaporation in the lungs ($q_{Lung}$) must likewise be replaced with the heat of evaporation in the air ($q_{Air}$). The modified formula for calculating the partial pressure now reads:

$$PAir = \frac{rF_{Air}}{100[\%]} \cdot po \cdot e^{qAir \cdot 427 \left[\frac{kp \cdot m}{kcal}\right] \frac{T_A - To}{Rd \cdot To \cdot T_A}} \quad (21)$$

The evaporative-respiratory heat losses can now be calculated with the equations shown above. The parameters are used for the determination as for the calculation of the convective-respiratory losses. A value of about 10.8 W is thus obtained.

About 13.1 W is then obtained by the calculations for the total heat loss via the respiratory tract.

However, a certain percentage of heat, which is stored in the upper airways during spontaneous breathing, during the ward phase, induction phase and wake-up phase, must now be subtracted from the calculated values Pconvresp and Pevaresp, because the heat and humidity exchange acts in the throat-pharyngeal cavity.

According to estimates, air is expired through the nose and mouth at a temperature of 30° C. This air still has a temperature of nearly 34° C. in the pharyngeal cavity and it is approximately 37° C. in the lungs. It thus becomes clear that heat is stored on the way from the lungs to the environment.

The absolute humidity decreases at an expiration temperature of 30° C. from 41 $g_{water}$ per $kg_{air}$ to 30 $g_{water}$ per $kg_{air}$, so that about 25% less air must be humidified. If this 25% is now subtracted from the calculated heat loss, a loss of 9.825 W is obtained, which will then correspond to a water release of 353 mL.

The analytical and physical equations are used for the calculation of the respiratory water release selected for the simulation program lead to acceptable values.

Perspiration

The sensible perspiration is an additional function of the heat release mechanisms. It develops when the other methods (convection, conduction, radiation and evaporation) are no longer sufficient to reduce the elevated temperature to the normal value.

Distinction is made in this type of water release between thermal and emotional perspiration. The paradoxical situation of pronounced cutaneous vasoconstriction in the area of the hands and feet (with corresponding cooling) takes place in case of intense psychological tension, e.g., due to stress, along with a simultaneous sweat section on the palmar and plantar surfaces. Intensified perspiration of the apocrine sweat glands (e.g., armpits) may also be associated herewith. By contrast, secretion is associated, as expected, with vasodilatation in the case of thermal perspiration, which is the only type of perspiration being taken into account here.

Since only the minimal (a human being loses at least 100 mL of sweat per day) and maximal (10 L to 12 L per day) sweat productions are stated in the literature, only two loss values and a control limit can be integrated in the simulation as well.

As long as the current core temperature is below the temperature set point set, the patient loses about 2.8 W. As soon as the temperature set point has been exceeded by 0.2° C., up to a maximum of 335 W can be lost.

To reach these transpiration values, the rate of perspiration must be multiplied by the heat of evaporation ($\lambda$=575: [kcal/$kg_{water}$]) and divided by the conversion factor 0.86 (from kcal/hr to W).

$$\text{Transpiration} = \frac{\text{min\_perspirationrate\_per\_day} \cdot \lambda}{24 \cdot 0.86} \quad (22)$$

Evaporation of Disinfectant from the Skin

Patients are disinfected with liquids (alcohol or iodine) during operations. The surface of the skin is moistened by the application of these disinfectants. Heat is then additionally removed from the body during the evaporation of these liquids.

However, since the disinfected surface is not too large and the disinfectants are not applied to the patient by the liter but in quantities of 1 g to 2 g only, the evaporation times are very short and the heat losses occurring in this connection can be ignored.

It can be seen from the following calculation:

$$P = m_{Disinfectant} \cdot \lambda_{Disinfectant} / t \quad (23)$$

in which $m_{Disinfectant}$: [g] quantity of disinfectant,
$\lambda_{Disinfectant}$: [kcal/kg] heat of evaporation
t: [sec] evaporation time that if the quantity of disinfectant is about 1 g of alcohol with a heat of evaporation of 210 kcal/kg (the corresponding value for water is 575 kcal/kg) and an evaporation time of 60 sec, only 14 W of heat are consumed for the evaporation of the disinfectant and no noticeable effects on the patient's temperature course will consequently occur.

Release of Heat Via Wounds

Besides the heat losses due to radiation, convection, conduction and evaporation, which are always present, as well as the additional heat release due to evaporation of disinfectants, the body releases more heat via the mucosa during operations with open wounds.

The releases in case of open wounds can be determined by means of Equation 8 (calculation of the transepidermal losses of evaporation).

However, the value for the skin must not be used here for the coefficient of permeability. To calculate the value of the loss, this coefficient must be assumed to be very high. Since the protecting, insulating skin is no longer present during the operation and the heat is released now directly by the mucosa, a transport coefficient of 20 g/(h m² kPa) is postulated here. (With protecting skin, this value is 4.575 g/(h m² kPa)) according to Fanger and Inouye.) One reason that this type of heat loss can be ignored is the usually small areas of the open wounds. There are only few surgical procedures now in which the skin is opened over a large area.

A heat loss of 1.9 W is obtained according to $$Ptwl = k \cdot Awound \cdot \left(ps - \frac{TrF}{100} \cdot pa\right) \cdot \frac{2400}{3600} \tag{24}$$

for a wound with an area of 400 cm² (Awound) and the above-mentioned high coefficient of permeability of the skin for an ambient temperature of 23° C., a skin temperature of 33° C. and a humidity of 50% in the air.

Compared to the continuous releases, this value is too low to cause an extreme change in the body temperature of adults and it is therefore ignored in the simulation program.

Heat Losses Due to Cold Infusions

Patients commonly receive a venous access during surgeries. Not only the anesthetics are administered via this access. In addition, one or more electrolyte fluids or even banked blood are administered to the patient during the entire phase of surgery. This access has, moreover, a protective function: The veins, via which important drugs could be injected in an emergency in a very short time, are kept "open" by the continuous injection of the infusions, because the veins can be punctured in case of a possible shock during the surgery with difficulty only or possibly not at all, so that the patient could die.

The anesthetics administered, which are stored mostly at a temperature of 7° C., bring about hardly any temperature changes in the body, because they enter the body in small quantities only.

The situation is different in the case of the electrolyte solutions and banked blood. Since they are injected in larger quantities, up to 2 L/hr. of crystalloid fluids or up to 6 L/hr. of blood depending on the surgery and duration, appreciable heat losses may occur during cold infusions. The releases that develop can be easily calculated in the knowledge of the following data, so that their contribution to hypothermia can thus be reduced as well. Based on the specific heat of water ($cinf_{Water}$=1: [cal/g °C.]), the heating of 1,000 mL of infusion solution by 1° C. requires about 1 kcal. The infusion of this quantity at a temperature of 20° C. consequently leads to a heat loss of 17 kcal, provided that the temperature of the fluid rises to 37° C. The heating of 1 L of blood from 8° C. to body temperature requires about 39 kcal. Since the human body has a specific heat ($cinf_{Blood}$) of 0.83 cal/g ° C., it can be calculated that an intraoperative heat loss of 60 kcal in a patient with a body weight of 70 kg lowers the mean body temperature by 1° C.: The infusion of 3.5 L at room temperature already leads to this loss. The heat losses due to infusion can be calculated from the following formula:

$$T_{end} = T_{start} - \frac{cinf_{Water} \cdot m_{Infu} \cdot (Tcore - T_{Infu})}{cinf_{Blood} \cdot m_{Pat}} \tag{25}$$

in which:
$T_{end}$: [° C.] patient's temperature after infusion,
$T_{start}$: [° C.] patient's temperature before infusion,
$T_{Infu}$: [° C.] temperature of infusion,
$m_{Infu}$: [mL] quantity of infusion
$m_{Pat}$: [kg] patient's body weight.

Since all heat data are expressed in the Watt unit in the simulation program, the losses due to cold infusion (Pinfu: [W]) are calculated here as follows:

$$Pinfu = \frac{\rho_{Blood} \cdot \text{Quantity\_of\_infusion} \cdot cinf \cdot (T_{infu} - Tcore)}{0.86} \tag{26}$$

The density of blood ($\rho_{Blood}$) has the value of 1,055 g/L. The quantity of infusion is stated in L per hour here.

If the patient has a body temperature of about 36° C. and 2 L of electrolyte solutions with a temperature of 23° C. (room temperature) are infused in the patient per hour, the patient will lose about 26 W of heat.

Description of the Physiological Model

Figure 3:
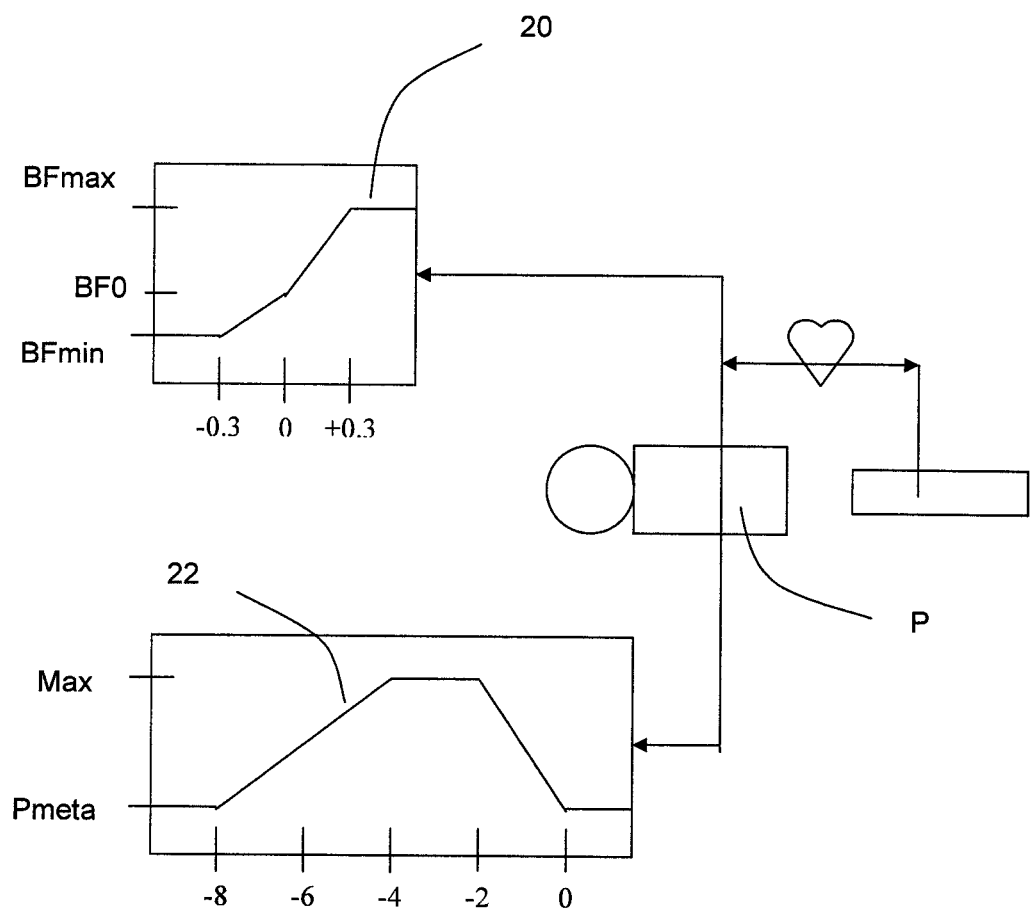
FIG. 3 is a view showing schematic model in case of intact heat regulation.

FIG. 3 schematically shows the schematic setup of the model, the blood flow and the temperature-dependent metabolic production. The upper part of FIG. 3 shows the blood flow 20 and the lower part shows the metabolism 22. The horizontal axis indicates a deviation from the body core temperature (Tcore) in ° C. The blood flow and the metabolic production, i.e., the manipulated variables for regulating the temperature balance, are dealt with more accurately in the simulation program.

A model and its response in a simulation program to temperature changes will be described below. More specifically, the blood flow and metabolic production, i.e., manipulated variables for regulating the temperature balance, will be examined.

The model used in the simulation program comprises a body core, a body periphery and the corresponding body shells. The head and upper body belong here to the core, which includes 60% of the total body mass. The periphery is composed of the four extremities.

94% of the heat for the body is produced in the upper body and head mainly by the metabolism. The remaining 6% is produced by the periphery. However, since this small percentage is not sufficient to automatically maintain the normal extremity temperature of about 32° C., warm blood is permanently flowing from the core into the periphery. The permanent, normal blood flow is described by BF0 in the simulation program. If the body temperature is in the range of the temperature set point, about 20 mL of heated blood flow into the extremities per 1,000 g of body weight (BW) per minute. However, as soon as the core temperature rises or the vasodilation begins under the effect of anesthetics, the blood flow increases in the model. This blood flow increases to a maximum of 100 mL of warm blood per 1,000 g of BW per minute (BFmax). It is reached as soon as the current body core temperature is greater than the set point by 0.3° C. or when the effect of anesthesia has started. If the body temperature drops due to increased release of heat or due to reduced heat production, the blood circulation becomes centralized to the upper body, and the warm blood is maintained increasingly in the core. At a temperature drop by 0.3° C. of the set point, with intact heat regulation, only 10 mL of blood (BFmin) will then flow to supply the arms and legs with oxygen, which will thus slowly cool. With heat regulation switched off, during the anesthesia, vasoconstriction again begins at a certain core temperature, so that the warmed blood is maintained in the thorax and head here as well and only a small amount is released into the periphery.

The values indicated for the quantities of transported blood can possibly be determined anew by measurements by means of the ultrasound Doppler effect on the femoral artery and modified in the simulation program.

Equations were derived now for the simulation program from the diagram for the blood flow.

As long as the core temperature is lower than or equal to the temperature set point (Tkset=36.7: [° C.]) minus the range of control (here 0.3° C.), the minimum quantity of blood flows. If the body temperature is in the range of −0.3 to 0 in the above diagram (temperature set point−range of control<core temperature<temperature set point), the blood flow (BF) is calculated as follows:

$$BF = \frac{BF0 - BF\min}{\text{Range\_of\_control}} \cdot Tk + BF0 - \frac{Tkset \cdot (BF0 - BF\min)}{\text{Range\_of\_control}} \quad (27)$$

The blood flow can thus be determined for the section Tkset≤Tk<Tkset+Range_of_control:

$$BF = \frac{BF\max - BF0}{\text{Range\_of\_control}} \cdot Tk + BF0 - \frac{Tkset \cdot (BF\max - BF0)}{\text{Range\_of\_control}} \quad (28)$$

As soon as the core temperature has reached and exceeded the set point plus range of control, the maximum quantity of blood (BFmax) flows from the core into the periphery.

Five different functions were set up for the case in which the heat regulation is intact (the patient is not under anesthesia). As long as Tkset−12≤Tcore<Tkset−3, $$Pprod = \frac{11}{20} \cdot (Tcore - Tkset - 17)^2 - 20 + Pmeta \quad (29)$$

applies to the production (Pprod).

The instantaneous metabolism is calculated for Tkset−3≤Tcore<Tkset−1 as follows:

$$Pprod = -10 \cdot (Tcore - Tkset - 2)^2 + 98 + Pmeta \quad (30)$$

Pprod can be determined in the range of Tkset−1≤Tcore<Tkset−0.5 as follows:

$$Pprod = -30 \cdot Tcore + 1.168 \cdot 10^3 + 30 \cdot (Tkset - 37) + Pmeta \quad (31)$$

The equation for the fourth section, Tksol−0.5≤Tcore<Tkset, is as follows:

$$Pprod = -146 \cdot Tcore + 5.402 \cdot 10^3 + 146 \cdot (Tkset - 37) + Pmeta \quad (32)$$

When the core temperature is equal to or greater than the temperature set point indicated, the body produces its basic metabolism Pmeta only.

With production switched off, i.e., when the patient is being anesthetized, the production drops to about 70% of the basal metabolic rate. Now, $$Pprod = 0.7 \cdot Pmeta \quad (33)$$

The basal metabolic rate (Pmeta), which is important for the calculation of metabolism, can be calculated differently for children, women and men. There is a weight- and age-dependent formula for determining the metabolic production for children. Different methods are available for determining the RMR (Resting Metabolic Rate) for adults. However, one must be aware of the fact that these are mostly estimates with a certain error margin. Exact values are obtained ultimately only by a calorimetric determination of the basal metabolism. Nevertheless, the results of the usual estimation methods yield definitely useful values. The basal metabolism can thus be determined for men as follows:

$$Pmeta = (10 \cdot G + 625 \cdot H - 5 \cdot age + 5) \cdot \frac{100.8952}{24 \cdot 86} \quad (34)$$

The resting metabolic rate of women is lower than the RMR of men by about 10%. The equation for this is:

$$Pmeta = (10 \cdot G + 625 \cdot H - 5 \cdot age - 161) \cdot \frac{100.8952}{24 \cdot 86} \quad (35)$$

in which G is the body weight in kg, H is the body size in cm$^2$ and age is the age in years.

After a more thorough examination of Ultmann's equation for determining the metabolism for children, it is noted that this formula may only be used for premature babies up to an age of about 30 days. The results have a very great error in case of older children with normal body weight. When calculating the heat production with the following parameters: 6 kg body weight and age 10 months, the child would have a basal metabolism of about 33 W.

Since premature babies shall not be specifically dealt with in the simulation program and results are unambiguously too high for infants older than 1 month, the metabolism for children is determined in the later program according to the formula for women, taking the corresponding age into account. The formula consequently reads as follows:

$$Pmeta = (10 \cdot G + 625 \cdot H - 5 \cdot age/12 - 161) \cdot \frac{100.8952}{24 \cdot 86} \quad (36)$$

The age is divided here additionally by 12 only, because the age is entered in months for children and in years for adults.

Thus, the heat production and release were described by formulas in the previous considerations. Another closer scrutiny of the formulas for the heat losses remarkably shows that most of the energy losses (Pradiation, Pconvektion, Ptwl are dependent on Tkskin and Tpskin, i.e., the shell temperatures.

The shell temperature is not always defined as the skin temperature here. As soon as the patient is unclothed, the value for Tkskin and Tpskin may, however, be considered to be the skin temperature.

When the patient is clothed or if different therapeutic measures are employed, these data are external temperatures of the materials used, which will then release the heat still present to the environment.

The conductivity of the skin tissue and of the insulating materials used, the core temperature and the peripheral temperature, as well as the values of the three heat releases mentioned are needed to determine these shell temperatures. The conductivity of the skin, $K_{Tissue}$, equals 45 W/(m²/K). The thermal conductivity is calculated from the "clo" value entered [(m² K)/W] for the additional insulation. The equation for the determination of the leitwert K: [W/m² K] reads:

$$K = \frac{1}{0.155 \cdot clo} \quad (37)$$

Data on individual insulation values can be found in the ISO standard 7730:1995 [6]. Values for special surgical cloths would have to be determined by measurements in advance. The values from the said standard are sufficient for general work with the simulation program.

The temperatures of the core (Tcore) and of the extremities (Tperi) are still needed now for determining the shell values.

The value for the thorax and head is obtained when all heat losses via the core are added to 94% of the total heat produced, the heat transport from the core into the periphery is subtracted, multiplication is carried out with the reciprocal value of the specific heat of the core and the value of $Tcore_{n-1}$ is added.

$$Tcore_n = \qquad (38)$$
$$\frac{1}{C_{Core}} \cdot \left( 0.94 \cdot Pprod - Pkzup + PconvK + PcondLK + PevaK + PradK + Pinfu + Trasnpiration \cdot \frac{aCore}{100} \right) + Tcore_{n-1}$$

The temperatures for the arms and legs can be calculated according to the following equation:

$$Tperi_n = \frac{1}{C_{Peri}} \cdot \left( 0.06 \cdot Pprod - Pkzup + PconvP + PcondP + PevaP + PradP + Trasnpiration \cdot \frac{(100 - aCore)}{100} \right) + Tperi_{n-1} \quad (39)$$

The heat losses via the periphery, equaling 6% of the heat, are subtracted. The heat removed from the core via the blood is attributed to the extremities in this formula.

The shell temperature of the core (Tkskin) and of the periphery (Tpskin) is now determined with the values calculated before:

$$Tkskin = Tcore_{n-1} + \qquad (40)$$
$$\left( \frac{1}{K_{Core}} + \frac{1}{K_{Tissue}} \right) \cdot \left( \frac{Pconv\ K_{n-1} + PradK_{n-1} + PtwlK_{n-1}}{A \cdot \frac{aCore}{100} \cdot \frac{qConv}{100}} \right)$$

$$Tpskin = Tpern_{n-1} + \qquad (41)$$
$$\left( \frac{1}{K_{Peri}} + \frac{1}{K_{Tissue}} \right) \cdot \left( \frac{Pconv\ K_{n-1} + PradK_{n-1} + PtwlK_{n-1}}{A \cdot \frac{aPeri}{100} \cdot \frac{qConv}{100}} \right)$$

It is seen in the equations that the respiratory component is missing from the heat losses via evaporation. In addition, the release by conduction is not integrated in the equations. However, as was already explained, the heat exchange by convection and radiation as well as the water losses via the skin take place in the body regions only with which the patient is lying on the operating table. Another thermal conductivity must be determined for the other component. It is composed of the conductivity of the skin and the insulation value of the operating mattress.

It is assumed for the simulation program that the beds on wards and in the wake-up room have a thermal conductivity of 1 W/(m² K). If the patient is lying in the induction room on an operating table with integrated mattress heater and the latter is also used, it is assumed that a gel substrate with a very high conductivity of 14 W/(m² K) is additionally located under the patient. If the conductive heat supply (mattress heater) is not in operation, the thermal conductivity for the foam mattress is 0.05 W/(m² K).

While specific embodiments of the invention have been shown and described in detail to illustrate the application of the principles of the invention, it will be understood that the invention may be embodied otherwise without departing from such principles.

What is claimed is:

1. A device for predicting or simulating a body temperature of a patient at a point in time that is in the future, the device comprising:
   a parameter value means for determining parameter values concerning one of the patient and the environment thereof; and
   a computing means for simulating a body temperature of the patient over a future period, based on established physical relationships between the parameters and heat transferred between the patient and the environment;
   a body temperature detecting means for detecting a body temperature of the patient, said computing means using the detected body temperature of the patient for further simulating the body temperature;
   a comparing means for comparing the detected body temperature with the simulated body temperature.

2. A device in accordance with claim 1, further comprising an output means for outputting results of one of the determination, simulation and comparison.

3. A device in accordance with claim 1, further comprising: heating means for heating the patient;
   a heating control means for controlling or regulating said heating means based on preset set points.

4. A device in accordance with claim 1, further comprising: heating means for heating the patient; a heating control means for controlling or regulating said heating means based on one of preset set points and characteristics.

5. A device in accordance with claim 1, wherein:
   said computing means determines an acceptable temperature range of the patient;
   said comparing means determines if the simulated body temperature of the patient is within, or outside, the acceptable temperature range;
   a heating means for heating the patient; and a heating control means for controlling or regulating said heating means based on said comparing means to apply thermotherapy to the patient before said future period to have future body temperatures be within the acceptable temperature range.

6. A device in accordance with claim 1, wherein:
said body temperature detecting means measures the actual temperature of the patient during a time period over which the body temperature is simulated and generates actual temperature values occurring during said time period;
said comparing means compares the simulated body temperature for the time period and the actual temperature values measured during the time period, said comparing means generating a thermotherapy signal to compensate for a difference between the future body temperature and the actual temperature value at time points during the time period;
said computing means uses the actual temperature values occurring during said time period for further simulation of the body temperature of the patient.

7. A device in accordance with claim 1, wherein:
at least one of said parameters is a non-temperature parameter;
said computing means generates a desired present temperature value for the patient based on the future body temperature;
said comparing means compares the detected body temperature with the desired present temperature value;
an output means is provided for outputting results of one of the determination, simulation and comparison.

8. A thermotherapy system for a patient, the system comprising:
a parameter value device determining a plurality of parameter values for different parameters concerning one of the patient and the environment thereof, at least one of said parameters being a non-temperature parameter;
a computing device simulating a future body temperature of the patient over a time period extending into the future based on established physical relationships between the parameters and heat transferred between the patient and the environment, said computing device determining an acceptable temperature range of the patient, and comparing the future body temperature of the patient with said acceptable temperature range of the patient, said computing device generating a desired present temperature value for the patient based on the future body temperature;
a temperature measuring means measuring the actual temperature of the patient and generating an actual temperature value;
a regulator generating a thermotherapy signal before the time period extending into the future to have the future body temperature be within the acceptable temperature range;
a thermotherapy device receiving the thermotherapy signal, and applying thermotherapy to the patient with respect to the thermotherapy signal.

9. A thermotherapy system in accordance with claim 8, wherein:
said computing device uses physical and physiological models of the patient which relate the different parameters to the heat transfer of the patient to generate the desired temperature value for the patient.

10. A thermotherapy system in accordance with claim 8, wherein:
said computing device simulates blood flow through the patient to generate the future body temperature and the desired temperature value for the patient.

11. A thermotherapy system in accordance with claim 8, wherein:
said computing device simulates a metabolism of the patient to generate the future body temperature and the desired temperature value for the patient.

12. A thermotherapy system in accordance with claim 8, wherein:
one of the different parameters is a parameter describing the environment in which the patient is located.

13. A thermotherapy system in accordance with claim 8, wherein:
one of the different parameters is a heat radiation parameter.

14. A thermotherapy system in accordance with claim 8, wherein:
one of the different parameters is a convection parameter.

15. A thermotherapy system in accordance with claim 8, wherein:
one of the different parameters is a conduction parameter.

16. A thermotherapy system in accordance with claim 8, wherein:
the different parameters include one of an evaporation parameter, a perspiration parameter, a parameter involved with the evaporation of disinfectant from the skin of the patient, a parameter describing a release of heat via wounds of the patient, a parameter describing the heat transfer of the patient due to infusions, and a parameter separately relating to one of a core or periphery of the patient.

17. A thermotherapy system in accordance with claim 8, wherein:
said temperature measuring means measures the actual temperature of the patient during said time period and generates actual temperature values occurring during said time period;
said regulator receives the future body temperature simulated for the time period and the actual temperature values measured during the time period, said regulator generating a thermotherapy signal to compensate for a difference between the future body temperature and the actual temperature value at time points during the time period;
said computing device uses the actual temperature values occurring during said time period for further simulation of the body temperature of the patient.

18. A thermotherapy process for thermo-regulating a patient, the process comprising the steps of:
determining an acceptable temperature range of the patient;
determining a plurality of parameter values for different parameters concerning one of the patient and the environment thereof, at least one of said parameters being a non-temperature parameter;
simulating a future body temperature of the patient at a future time based on established physical relationships between the parameters and the temperature of the patient;
comparing the future body temperature of the patient with said acceptable temperature range of the patient;
determining if the future body temperature of the patient is within, or outside, the acceptable temperature range;
if the simulated future body temperature is outside of the acceptable temperature range, applying thermotherapy to the patient before said future time to have future body temperatures be within the acceptable temperature range.

19. A thermotherapy process in accordance with claim 18, wherein:
said simulating uses physical and physiological models of the patient which relate the different parameters to a body temperature of the patient.

20. A thermotherapy process in accordance with claim 18, wherein:
said simulating includes one of simulating blood flow through the patient, and simulating the metabolism of the patient.

21. A thermotherapy process in accordance with claim 18, wherein:
at least one of said different parameters is a parameter describing the environment in which the patient is located, a heat radiation parameter, a convection parameter, a conduction parameter, an evaporation parameter, a perspiration parameter, a parameter involved with the evaporation of disinfectant from the skin of the patient, a parameter describing a release of heat via wounds of the patient, a parameter describing the heat transfer of the patient due to infusions, or a heat radiation parameter.

* * * * *